United States Patent
Vogt (10) Patent No.: US 9,895,830 B2
(45) Date of Patent: Feb. 20, 2018

(54) METHOD FOR PRODUCING SPACERS AND DEVICE THEREFOR

(71) Applicant: HERAEUS MEDICAL GMBH, Wehrheim (DE)

(72) Inventor: Sebastian Vogt, Erfurt (DE)

(73) Assignee: HERAEUS MEDICAL GMBH, Wehrheim (DE)

(*) Notice: Subject to any disclaimer, the term of this patent is extended or adjusted under 35 U.S.C. 154(b) by 735 days.

(21) Appl. No.: 14/312,817

(22) Filed: Jun. 24, 2014

(65) Prior Publication Data
US 2015/0001765 A1   Jan. 1, 2015

(30) Foreign Application Priority Data
Jun. 26, 2013  (DE) ............ 10 2013 010 593

(51) Int. Cl.
| | | |
|---|---|---|
| B29C 39/00 | (2006.01) | |
| A61F 2/38 | (2006.01) | |
| B29K 33/00 | (2006.01) | |
| A61F 2/30 | (2006.01) | |
| A61F 2/46 | (2006.01) | |

(52) U.S. Cl.
CPC ............ *B29C 39/003* (2013.01); *A61F 2/389* (2013.01); *A61F 2/3094* (2013.01); *A61F 2002/30672* (2013.01); *A61F 2002/30957* (2013.01); *A61F 2002/4653* (2013.01); *A61F 2240/004* (2013.01); *A61F 2310/00353* (2013.01); *B29K 2033/12* (2013.01)

(58) Field of Classification Search
CPC .................................................. B29C 39/003
See application file for complete search history.

(56) References Cited

U.S. PATENT DOCUMENTS
| | | | | |
|---|---|---|---|---|
| 2009/0157189 A1* | 6/2009 | Hartman | ............ | A61F 2/30 623/18.11 |
| 2012/0330435 A1* | 12/2012 | Engqvist | ............ | A61B 17/8085 623/23.61 |

FOREIGN PATENT DOCUMENTS
| | | | |
|---|---|---|---|
| DE | 10 2011 104 808 A1 | 12/2012 | |
| EP | 2 526 900 A1 | 11/2012 | |
(Continued)

OTHER PUBLICATIONS
German Office Action dated Sep. 23, 2013.
European Search Report dated Feb. 5, 2015.
Canadian Office Action dated Jul. 10, 2015.

*Primary Examiner* — Larry Thrower
(74) *Attorney, Agent, or Firm* — Norris McLaughlin & Marcus P.A.

(57) ABSTRACT

The invention relates to a method for producing spacers from a bone cement comprising the following chronological steps:
A) controlling the temperature of a casting mold to a first temperature;
B) filling a cement dough, which has a temperature that is lower than the temperature of the temperature-controlled casting mold, into the temperature-controlled casting mold;
C) allowing the cement dough to cure in the casting mold to form a spacer; and
D) separating the casting mold from the spacer after the spacer is cured.

The invention also relates to a device for producing spacers from a bone cement through said method comprising a casting mold and a temperature control facility for controlling the temperature of the casting mold, whereby at least 80% of the inner surface of the casting mold comprises a negative image of the spacer surface to be produced.

12 Claims, 4 Drawing Sheets

(56) References Cited

FOREIGN PATENT DOCUMENTS

EP   2 532 323 A1   12/2012
WO   2008/088869 A1   7/2008

* cited by examiner

Figure 3 (produced through a method other than the inventive method)

Figure 4 (produced through a method according to the invention)

METHOD FOR PRODUCING SPACERS AND DEVICE THEREFOR

The invention relates to a method for producing spacers from a bone cement and to a device for producing spacers from a bone cement through said method.

Accordingly, the subject matter of the invention is a method for producing largely pore-free polymethylmethacrylate spacers (PMMA spacers) for use as temporary spacer in the scope of two-stage septic revision surgeries of articular endoprostheses.

BACKGROUND OF THE INVENTION

Articular endoprostheses currently have a service life of several years, for example on average more than ten and up to fifteen years in the case of cemented hip endoprostheses. However, undesirable loosening of the articular endoprostheses can occur before the end of the usual service life. This can concern either septic or aseptic loosening. Aseptic loosening means that no microbial germs are detectable yet. There are many causes of aseptic loosening. Aseptic loosening is often related to abrasion at the sliding surfaces of articular endoprostheses. The loosening process in septic loosening is induced by microbial germs. This can either be early or late infections depending on the time of manifestation. Septic loosening is a very serious disease for the patient and associated with high additional costs. It is customary to perform a revision surgery in cases of aseptic and septic loosening alike. This can proceed as a one-stage or a two-stage revision surgery. Two-stage revision surgeries are very common in cases of septic loosening.

In a two-stage revision surgery, the infected articular endoprosthesis is removed in a first surgery (OP) followed by debridement and subsequent insertion of a temporary place-holder, a so-called spacer. Said spacer occupies for a number of weeks the space previously occupied by the revised endoprosthesis until the manifest infection has subsided. Said place-holder function is very important in order to effectively prevent muscular atrophy during this period of time and in order to stabilise the existing resection scenario. There are non-articulated and articulated spacers available. Articulated spacers or joint spacers replicate the function of the joint and allow the afflicted limbs to have a certain degree of mobility. This allows the patient to be mobilised early. Articulated spacers are current the state of the art. The spacer is removed in a second surgery, another debridement is done before implanting a cemented or cement-free revision articular endoprosthesis.

The use of spacers is originally based on the work of Hovelius and Josefsson (Hovelius L, Josefsson G (1979), "An alternative method for exchange operation of infected arthroplasty", Acta Orthop. Scand. 50: 93-96). Other early work on spacers includes Younger (Younger A S, Duncan C P, Masri B A, McGraw R W (1997), "The outcome of two-stage arthroplasty using a custom-made interval spacer to treat the infected hip", J. Arthroplasty 12: 615-623), Jones (Jones W A, Wroblewski B M (1989), "Salvage of failed total knee arthroplasty: the 'beefburger' procedure", J. Bone Joint Surg. Br. 71: 856-857), and Cohen (Cohen J C, Hozack W J, Cuckler J M, Booth R E Jr (1988), "Two-stage reimplantation of septic total knee arthroplasty, Report of three cases using an antibiotic-PMMA spacer block", J. Arthroplasty 3: 369-377). McPherson described a concept according to which spacers can be manufactured from bone cement exclusively (McPherson E J, Lewonowski K, Dorr L D (1995), "Techniques in arthroplasty. Use of an articulated PMMA spacer in the infected total knee arthroplasty", J. Arthroplasty 10: 87-89).

Spacers equipped with antibiotics for temporary replacement of knee, hip, and shoulder endoprostheses are available on the market. It is disadvantageous though that the antibiotics contained therein are pre-determined and cannot be adapted specifically to suit the antibiogram of the microbial germs found to be present.

Spacers are often shaped from cement dough by the physician in the course of a surgery or are cast by the physician using elastic silicone moulds. Alternatively, industrially produced spacers have been commercially available in a range of standard sizes for a number of years. Said pre-made spacers can be implanted directly by the physician without any major preparatory work, whereby the spacers are usually fixed to the bone tissue with polymethylmethacrylate bone cement. The advantage of industrially produced spacers is that the surface quality of the sliding surfaces of the pre-made spacers is generally markedly better as compared to the spacers produced intra-operatively. The sliding surfaces are the surfaces of articulated spacer parts that slide on each other or roll over each other in order to replicate the function of a joint by the spacer. Moreover, using pre-made spacers can save valuable surgery time and simplifies the entire surgical process markedly since the time-consuming and laborious step of spacer production is omitted.

Casting spacers with polymethylmethacrylate bone cement using elastic casting moulds, such as, for example, silicone moulds, leads to spacers having a relatively good surface quality. However, it is an inherent problem of industrial production that casting moulds made of rubber-elastic material are sensitive to wear and tear and are therefore not suitable for the production of spacers in large quantities. Moreover, the production of silicone moulds is expensive. It is therefore reasonable to use casting moulds that are largely resistant to wear and tear.

Our own casting experiments using wear-resistant casting moulds made of metal or non-rubber-elastic plastic materials and polymethylmethacrylate bone cement dough at room temperature showed that irregular pore-like depressions are formed on the surface of the spacers. These pores and/or surface defects are particularly bothersome in the region of the sliding surfaces. Pores or other irregularities on the sliding surfaces can lead to increased abrasion while the spacer is implanted in the patient, which might later favour or trigger inflammatory processes if the abraded material is not removed during explanation of the spacer. Moreover, pores and other surface defects can act as fissure initiation points and thus adversely affect the mechanical stability of the spacers. It is feasible to reduce or eliminate pores and other surface defects by grinding and polishing. This type of reworking is time-consuming and expensive, though.

Accordingly, it is the object of the invention to overcome the disadvantages of the prior art. In particular, a method and a device for producing spacers from bone cement, in particular polymethylmethacrylate bone cement, are to be developed that can be used with wear-resistant, dimensionally stable casting moulds to produce spacers on an industrial scale, whereby the formation of pores or other surface defects is largely excluded.

SUMMARY OF THE INVENTION

The objects of the invention are met by a method for producing spacers from a bone cement comprising the following chronological steps:

A) controlling the temperature of a casting mould to a first temperature;

B) filling a cement dough, which has a temperature that is lower than the temperature of the temperature-controlled casting mould, into the temperature-controlled casting mould;

C) allowing the cement dough to cure in the casting mould to form a spacer; and

D) separating the casting mould from the spacer after the spacer is cured.

DETAILED DESCRIPTION

The casting mould can be temperature-controlled further while the bone cement is being cured. If the heat capacity of the casting mould is sufficient, it can just as well be sufficient for the casting mould to have been temperature-controlled while the bone cement was filled into it. For the latter, it is sufficient, for example, if a casting mould made of stainless steel has a wall thickness of at least one milimeter.

A method according to the invention can provide a cement dough made of polymethylmethacrylate (PMMA) to be used as cement dough, preferably a polymethylmethacrylate-containing cement dough that has been degassed by vacuum action, and the spacer thus produced to consist of polymethylmethacrylate.

Said bone cements are particularly well-suited for implementing the method according to the invention. Moreover, spacers formed from said bone cements show high biocompatibility.

Moreover, the invention can provide at least the casting mould surface forming the spacer to consist of at least 90%, preferably at least 99% of a non-elastic material, preferably of polyethylene, polypropylene, polyamide and/or stainless steel, with stainless steel 1.4401 and/or stainless steel 1.4404 being particularly preferred.

Said materials are dimensionally stable to a sufficient degree and can be detached well from the spacers and/or spacer parts thus produced even if they are re-used.

A preferred refinement of the invention proposes the cement dough to be filled into the temperature-controlled casting mould while it has a temperature at least 10° C. lower than the first temperature of the temperature-controlled casting mould, preferably a temperature at least 20° C. lower, particularly preferably 20° C. to 50° C. lower than the first temperature of the temperature-controlled casting mould.

These temperature differences ensure that directional curing of the bone cement initiating at the inner surface of the casting mould proceeds.

The invention can just as well provide the casting mould to be temperature-controlled to a first temperature between 40° C. and 65° C., preferably between 45° C. and 60° C., particularly preferably between 50° C. and 55° C.

Said temperatures are particularly well-suited for initiating the polymerisation process of the PMMA bone cements, which are used preferably. Therefore, it is particularly preferred for the casting moulds to be at said temperatures.

Moreover, it is particularly advantageous to provide that the cement dough being filled into the casting mould has a temperature between −20° C. and 30° C., preferably between −20° C. and 10° C., particularly preferably between −20° C. and 0° C.

This reduces the curing of the bone cement, in particular the polymerisation of the PMMA bone cement, in the interior such that directional curing from outside will proceed.

A refinement of the invention proposes that the cement dough is brought to a temperature lower than the first temperature of the temperature-controlled casting mould before filling it into the casting mould.

Active temperature-control of the cement dough renders the procedure of the method according to the invention more reproducible, the method can be standardised and is thus more amenable to mass production.

The invention can preferably provide that the cement dough being filled into the casting mould has a volume that is at least 2% by volume larger, preferably at least 5% by volume larger, than the mould cavity, whereby the additional volume is present in a sprue of the casting mould at least before the bone cement is cured.

This allows shrinkage of the bone cement during the curing process to be compensated.

Moreover, the invention can preferably provide that at least one steel core is placed into the casting mould for reinforcement of the spacer, whereby the temperature of the steel core is at least 10° C. lower than the first temperature of the temperature-controlled casting mould, preferably at least 30° C. lower than the first temperature of the casting mould.

This attains stabilisation of the spacer and/or spacer part. Controlling the temperature of the steel core prevents the polymerisation and/or the curing of the bone cement to proceed from the steel core outwards. Preferably, the steel core has the same or a lower temperature as/than the cement dough.

The invention can provide in this context that the at least one steel core is suspended appropriately in the casting mould by means of separators such that the distance between the internal surface of the casting mould and the surface of the steel core is defined, whereby the separators have a temperature that is at least 10° C. lower than the first temperature of the temperature-controlled casting mould, preferably at least 30° C. lower than the first temperature of the temperature-controlled casting mould.

Having the separators allows the steel core or the steel cores to be arranged at a defined position in the spacer. In this context, controlling the temperature of the separators prevents them from acting as seeds and/or initiation points for the polymerisation and/or the curing of the bone cement. Preferably, the separators have the same or a lower temperature as/than the cement dough.

A refinement of the method according to the invention proposes that the bone cement contains at least one antibiotic and/or one antiseptic, whereby it is preferred for two antibiotics and/or antiseptics to be present and particularly preferred for three antibiotics and/or antiseptics to be present.

This renders the spacer suitable for fighting sites of infection.

The underlying objects of the invention are also met by a device for producing spacers from a bone cement through said method comprising a casting mould and a temperature control facility for controlling the temperature of the casting mould, whereby at least 80% of the inner surface of the casting mould comprises a negative image of the spacer surface to be produced.

In this context, the invention can provide the casting mould to consist of at least two parts that are mobile with respect to each other.

This allows the casting mould to be detached more easily from the fully cured bone cement.

The invention can just as well provide that the device comprises a bone cement reservoir and a filler neck that is connected to the bone cement reservoir and by means of which the casting mould can be filled with bone cement.

This makes it easier to fill the bone cement dough into the casting mould, in particular in case the entire process is automated.

Moreover, the invention can provide the casting mould to comprise at least one sprue into which excess bone cement can be taken up, preferably the casting mould comprises at least one riser, particularly preferably multiple risers, at the topmost regions of the casting mould for ventilating the inside of the casting mould.

Similar to casting moulds for metals, having the sprue ensures that there remains a reservoir of bone cement present if the volume of the curing bone cement is reduced such that no holes form in the spacer thus produced. The purpose of the risers is to prevent the inclusion of air in the casting mould which would otherwise lead to recesses in the spacer.

Finally, the invention can provide the temperature control facility to comprise an electrical resistance heating and/or a fluid heating which is or are present in the walls of the casting mould and/or is or are applied to the outside of the walls of the casting mould.

Alternatively, the temperature control facility can simply touch against the casting mould from outside or emit radiation onto the casting mould in order to heat the casting mould and thus provide for temperature control. Having a temperature control facility of this type allows automation of the method to be implemented in particularly easy manner.

The invention is based on the surprising finding that controlling the temperature of the casting mould allows to attain directional curing of the bone cement such that the surface of the spacer thus produced becomes smooth and level. In the method according to the invention, the cement dough solidifies from outside towards the inside such that still flowable bone cement can compensate for shrinkage of the curing bone cement such that a smooth spacer surface is produced by this means.

In this context, the invention is based on the surprising finding hat spacers having pore-free surfaces are obtained in casting with polymethylmethacrylate bone cement dough, if casting moulds made of non-rubber-elastic material are used which have previously been adjusted to a temperature of 40° C. or more, whereby the polymethylmethacrylate bone cement dough to be introduced into the casting mould has a temperature at least 10° C. lower than the casting mould.

In the scope of the present invention, it was found that the formation of pores and other surface defects during spacer production in non-rubber-elastic, dimensionally stable casting moulds is related to the polymerisation of the polymethylmethacrylate cement dough commencing on the inside of the spacer and proceeding with increasing self-acceleration due to the release of the polymerisation enthalpy. In the process, the polymethylmethacrylate cement dough cures from inside outwards in the direction of the wall of the casting mould. The polymerisation is associated with polymerisation shrinkage. This means that the curing cement dough retracts from the wall of the casting mould. In the process, the cement dough tears off unevenly which forms pores and other surface defects. The sprue is usually arranged in the middle of the casting mould. Since the polymerisation proceeds from inside outwards, no cement dough can be drawn out of the sprue for compensation of the polymerisation shrinkage since the central region of the cement dough in the middle about the sprue polymerises first and is therefore further along in the curing process than the cement dough in the region of the wall of the casting mould.

The radical polymerisation of the bone cement dough is strongly temperature-dependent. This means, the higher the temperature, the faster the polymethylmethacrylate bone cement dough cures. The rationale underlying the invention is to heat the casting mould appropriately such that the casting mould has a clearly higher temperature than the polymethylmethacrylate bone cement dough to be used for the casting. This accelerates the polymerisation at the internal surface of the casting mould. Accordingly, the cement dough polymerises from outside inwards. This means that the polymerisation shrinkage proceeds from outside inwards. This allows the shrinking polymethylmethacrylate bone cement dough to draw still flowable polymethylmethacrylate bone cement dough out of the sprue and/or the risers. This produces spacers having a smooth pore-free surface.

The exothermic radical polymerisation of the bone cement dough in turn produces the heat that causes the polymerisation to progress. The polymerisation is sparked through controlling the temperature of the casting mould on the inside walls of the casting mould and proceeds into the inside of the polymerising spacer by the release of heat during polymerisation. For this reason, there is no need to temperature-control the casting mould continuously since, figuratively speaking, the heat energy from the casting mould is needed just as a spark to initiate the self-maintaining polymerisation reaction.

The invention can be implemented, for example, through a method for producing polymethylmethacrylate spacers, in which a polymethylmethacrylate cement dough degassed through the action of a vacuum is filled into the at least one-part casting mould that is controlled to a temperature of 40° C. to 65° C. and contains at least one sprue and consists of a non-rubber-elastic material, whereby the temperature of the cement dough is at least 10° C. lower than the temperature of the casting mould, whereby the volume of the polymethylmethacrylate cement dough is larger by at least 2% by volume than the volume of the mould cavity, whereby, subsequently, the curing proceeds in the casting mould and the casting mould is separated from the polymethylmethacrylate spacer only after the polymethylmethacrylate spacer has cured.

BRIEF DESCRIPTION OF THE DRAWINGS

Further exemplary embodiments of the invention shall be illustrated in the following on the basis of four schematic figures, though without limiting the scope of the invention. In the figures.

Figure 1:
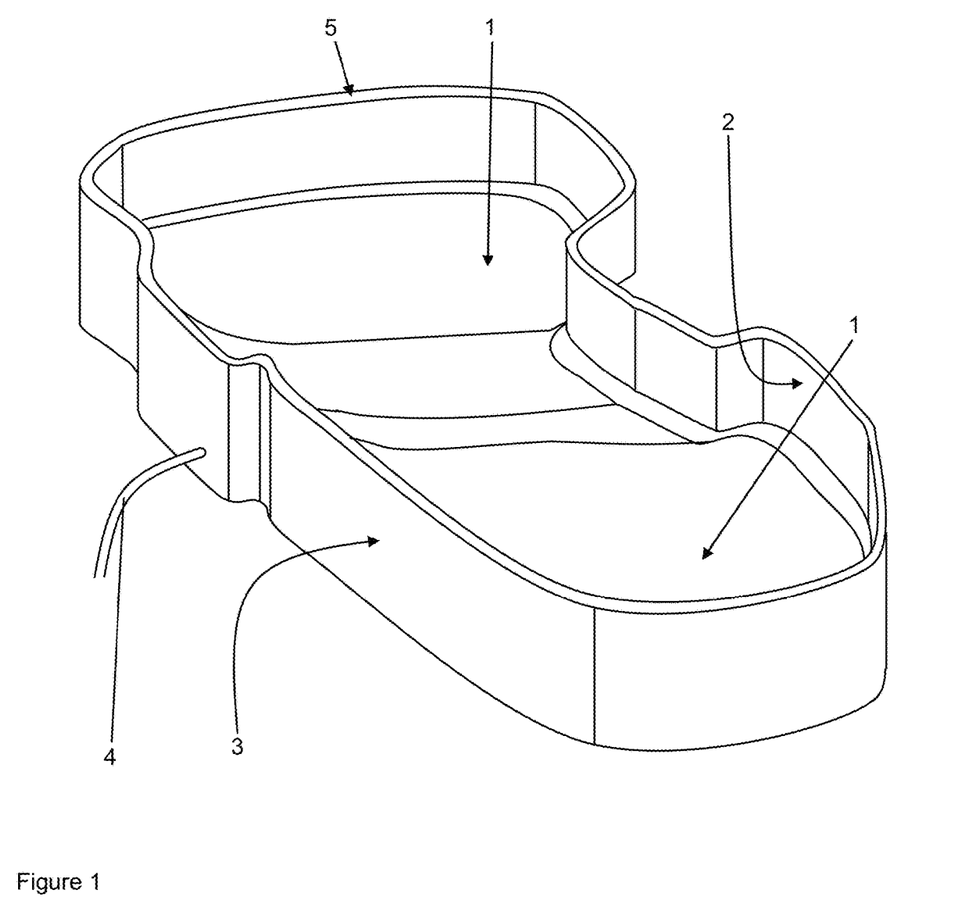
FIG. 1: shows a schematic perspective view of a lower part of a casting mould according to the invention for producing a tibial component of a knee spacer.
Figure 2:
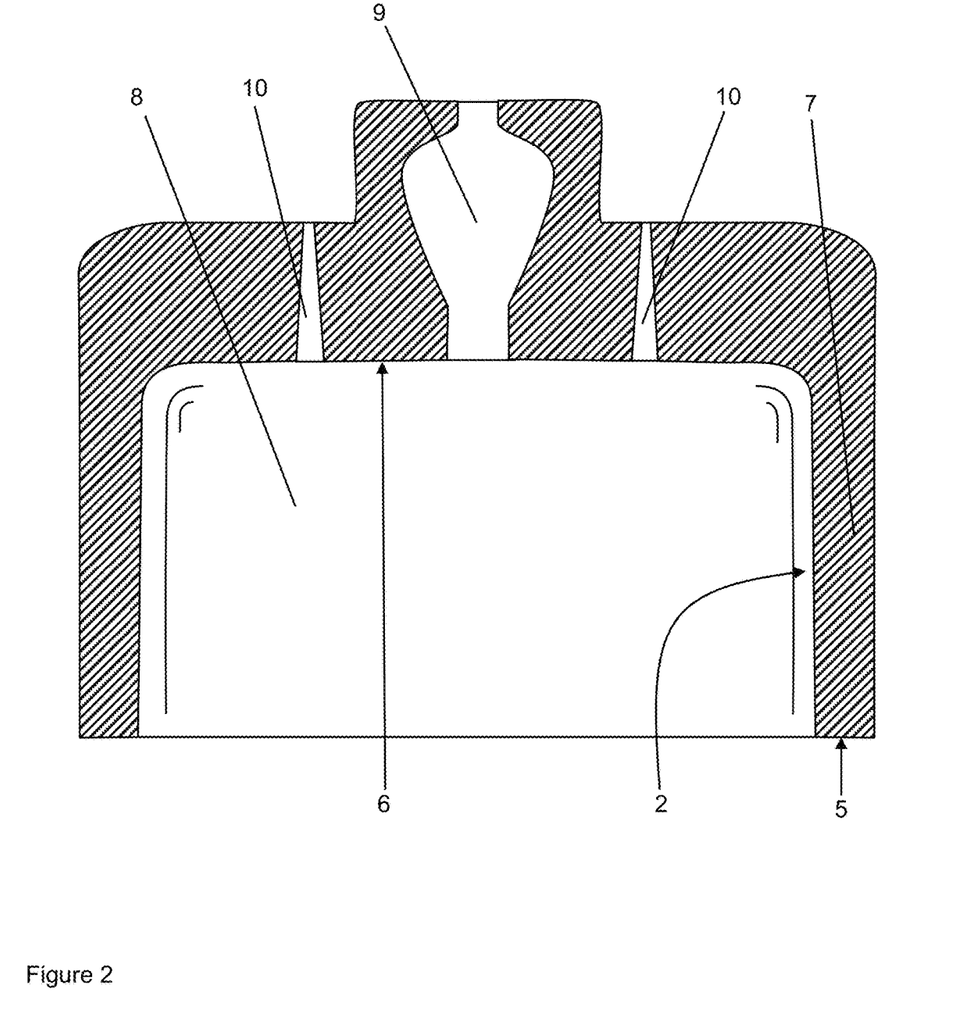
FIG. 2: shows a schematic cross-sectional view of an upper part of a casting mould according to the invention for producing a tibial component of a knee spacer.

FIG. 1 shows a schematic perspective view of a lower part of a casting mould according to the invention for producing a tibial component of a knee spacer, and FIG. 2 shows a schematic cross-sectional view of an upper part of a casting mould according to the invention for producing a tibial component of a knee spacer. When the two parts are assembled, they jointly form a two-part casting mould for a tibial component of a knee spacer.

The casting mould parts shown in FIGS. 1 and 2 are hollow moulds made of stainless steel. The lower casting mould part (FIG. 1) is structured in the manner of a container that is closed on the bottom and open on the top. The lower casting mould part comprises a floor surface 1 that is a negative image of the sliding surface of the tibial component of the mobile articulated knee spacer to be produced. The lower casting mould part is bordered on the sides by internal walls 2 which also are a negative image of the spacer shape to be produced.

A cable 4 projects from an external wall 3 of the lower casting mould part. The cable 4 contains all electrical leads that are connected to a heating wire (not shown) on the inside of the casting mould part. The heating wire and electrical leads are obviously electrically insulated with respect to the casting mould. Alternative to electrical heating of the casting mould part, instead of a cable 4, a hose 4 can be provided through which a heated fluid can flow for controlling the temperature of the casting mould. For this purpose, pipes (not shown) through which the heated fluid (for example, water) can flow are provided within the walls or on the external wall 3 of the casting mould. The heating fluid can be drained at another place by means of another hose (not shown).

The fluid heating or the electrical heating can be used to control the temperature of the casting mould. In order to adjust a definite temperature, a temperature sensor (not shown) can be provided in at least one place of the casting mould and is connected to a control unit or a control circuit (not shown) by means of which the heating power and/or the temperature and/or the flow rate of the heating fluid (for example, water) can be controlled and by means of which the temperature of the casting mould can thus be adjusted.

The upper edge of the lower casting mould part is formed by a planar connecting edge 5. The connecting edge 5 is to be placed on an upper casting mould part, as is shown in exemplary manner in FIG. 2. The connecting edge 5 is arranged in said place as lower side of a wall 7 of the upper casting mould part. The casting mould parts can be connected to each other by means of the connecting edges 5 in sealed and, at least on the inside, flush manner. Preferably, the casting mould parts can be connected fixedly to each other, for example by means of a detachable lock or a closure (not shown).

The upper casting mould part is bordered on the inside of the upper side by a ceiling surface 6, which is a negative image of the tibia-facing side of the spacer part. The inside walls 2, the floor surface 1 and the ceiling surface 6 thus form a mould cavity 8 for the spacer part to be produced, i.e. the tibial part of the two-part knee spacer.

The upper casting mould part, much like the lower casting mould part, can also be heated and/or its temperature can be controlled.

The ceiling surface 6 is interrupted by a sprue 9 and multiple risers 10 and is open towards the outside. The risers 10 and the sprue 9 are arranged in the topmost places within the assembled casting mould. The casting mould, assembled and temperature-controlled to 58° C., is filled through the sprue 9 with a PMMA bone cement (not shown) that is −18° C. cold and has been mixed in a vacuum. For this purpose, the bone cement can be taken from a conventional freezer or cooling unit. The risers 10 ensure that no air inclusions remain in the interior 8 of the casting mould.

Since the temperature of the internal walls 2, floor surface 1, and ceiling surface 6 is higher, polymerisation of the PMMA bone cement commences on said surfaces. Heat is released during the polymerisation and leads to progression of the polymerisation front into the interior of the curing bone cement inside the casting mould. This is associated with shrinkage of the curing bone cement. Bone cement to be drawn in through the sprue 9 for compensation of the shrinkage loss such that no hollow spaces are formed in the spacer and/or spacer part thus formed, and/or such that the surface of the curing bone cement does not detach from the internal surfaces 1, 2, 6 of the casting mould during the curing process.

As soon as the bone cement is fully cured, the two casting mould parts are detached from each other and the finished spacer and/or the finished spacer part can be taken out. Protrusions due to the risers 10 or the sprue 9 can be removed mechanically.

With regard to the bone cements and cartridges for mixing and dispensing bone cement to be used, reference shall be made to embodiments known from the prior art.

The exemplary embodiment shown by means of FIGS. 1 and 2 can be translated easily by a person skilled in the art to the femoral component matching the tibial component to form a two-part articulated spacer. However, the invention shall not be construed as to be limited to knee spacers. The same principle can also be used to produce other two-part or one-part spacers. For this purpose, it is simply necessary to adapt the inner shape of the casting mould parts (or of a one-part casting mould) to the bone to be replaced. The exemplary embodiment according to FIGS. 1 and 2 can therefore be translated easily to other spacers by a person skilled in the art.

Figure 3:
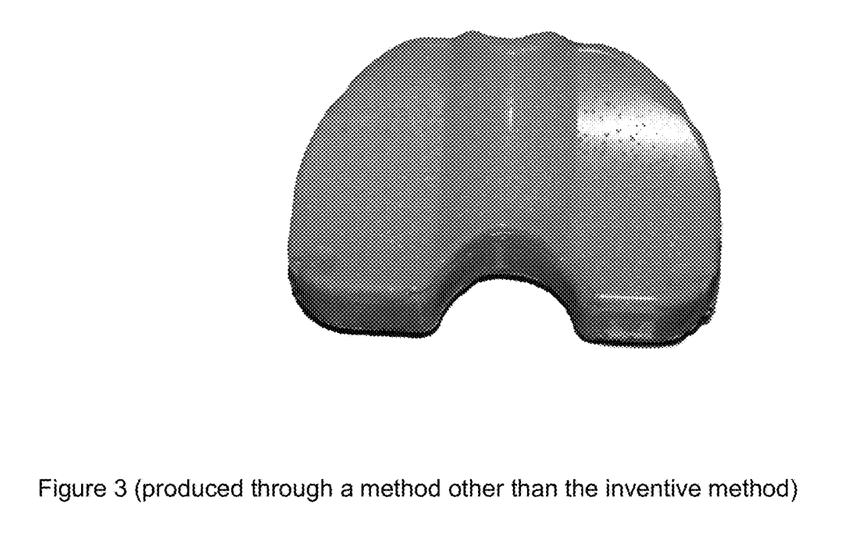
FIG. 3: shows an image of a tibial component of a knee spacer produced through a method other than the inventive method.

FIG. 3 shows an image of a tibial component of a knee spacer that was produced through a method using no temperature-controlled casting mould and non-elastic walls. The tibial component of the knee spacer was cast using a two-part polyethylene mould and Palacos® LV+G bone cement made by Heraeus Medical GmbH. The temperature of the polyethylene casting mould was 23° C. The temperature of the monomer liquid and of the cement powder of the polymethylmethacrylate bone cement also was 23° C. After the bone cement was cured, the tibial spacer was taken out of the mould. FIG. 3 shows the surface of the spacer part. Pores and other surface defects are clearly evident.

Figure 4:
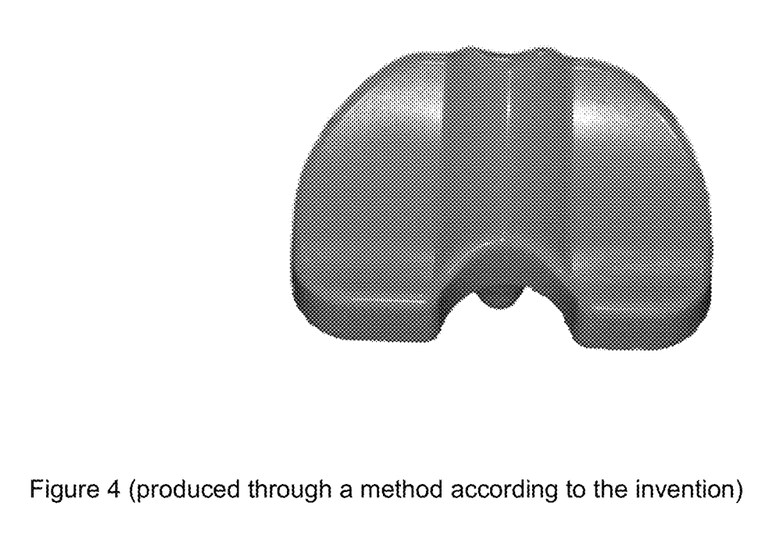
FIG. 4: shows an image of a tibial component of a knee spacer produced through a method according to the invention.

FIG. 4 shows an image of a tibial component of a knee spacer produced using a method according to the invention. The tibial component of the knee spacer was cast using a two-part polyethylene mould and Palacos® LV+G bone cement made by Heraeus Medical GmbH. The temperature of the polyethylene casting mould was 55° C. The temperature of the monomer liquid and of the cement powder of the polymethylmethacrylate bone cement was 23° C. After the bone cement was cured, the tibial spacer was taken out of the mould. FIG. 4 shows the surface of the spacer part. It is clearly evident that the spacer produced by this means no longer shows pores or other surface defects.

The features of the invention disclosed in the preceding description and in the claims, figures, and exemplary embodiments, can be essential for the implementation of the various embodiments of the invention both alone and in any combination.

LIST OF REFERENCE NUMBERS

1 Floor surface
2 Internal wall
3 External wall
4 Cable hose

5 Connecting edge
6 Ceiling surface
7 Wall
8 Mould cavity interior of the casting mould
9 Sprue
10 Riser

The invention claimed is:

1. Method for producing spacers from a bone cement, comprising the chronological steps of:
   A) temperature controlling a casting mould to a first temperature;
   B) filling a cement dough, which has a temperature that is lower than the temperature of the temperature-controlled casting mould, into the temperature-controlled casting mould;
   C) allowing the cement dough to cure in the casting mould to form a spacer; and
   D) separating the casting mould from the spacer after the spacer is cured.

2. Method according to claim 1, wherein said cement dough is made of polymethylmethacrylate, and the spacer thus produced is formed of polymethylmethacrylate.

3. Method according to claim 1 wherein at least the surface of the casting mould forming the spacer is comprised of at least 90% of a non-elastic material.

4. Method according to claim 1, wherein the cement dough is filled into the temperature-controlled casting mould while it has a temperature at least 10° C. lower than the first temperature of the temperature-controlled casting mould.

5. Method according to claim 1, wherein the casting mould is temperature-controlled to a first temperature between 40° C. and 65° C.

6. Method according to claim 1, wherein the cement dough being filled into the casting mould has a temperature between −30° C. and 30° C.

7. Method according to claim 1, wherein the cement dough is brought to a temperature lower than the first temperature of the temperature-controlled casting mould before filling it into the casting mould.

8. Method according to claim 1, wherein the cement dough being filled into the casting mould has a volume that is at least 2% by volume larger than the mould cavity, whereby the additional volume is present in a sprue (9) of the casting mould at least before the bone cement is cured.

9. Method according to claim 1, wherein at least one steel core is placed into the casting mould for reinforcement of the spacer, at a temperature of-at least 10° C. lower than the first temperature of the temperature-controlled casting mould.

10. Method according to claim 9, wherein the at least one steel core is suspended in the casting mould by means of separators such that the distance between the internal surface of the casting mould and the surface of the steel core is defined, whereby the separators have a temperature that is at least 10° C. lower than the first temperature of the temperature-controlled casting mould.

11. Method according to claim 1, wherein the bone cement contains at least one antibiotic and/or one antiseptic.

12. The method of claim 3, wherein said non-elastic material is selected from the group consisting of polyethylene, polypropylene, polyamide, stainless steel and combinations thereof.

* * * * *